US008725272B2

(12) United States Patent
Kimura et al.

(10) Patent No.: US 8,725,272 B2
(45) Date of Patent: May 13, 2014

(54) HIGH-FREQUENCY TREATMENT INSTRUMENT

(75) Inventors: Megumi Kimura, Tokyo (JP); Keita Suzuki, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 52 days.

(21) Appl. No.: 13/307,435

(22) Filed: Nov. 30, 2011

(65) Prior Publication Data

US 2012/0136424 A1    May 31, 2012

Related U.S. Application Data

(63) Continuation of application No. PCT/JP2010/063393, filed on Aug. 6, 2010.

(30) Foreign Application Priority Data

Sep. 15, 2009   (JP) ................................. 2009-212945

(51) Int. Cl.
*A61N 1/39*   (2006.01)
*A61N 1/00*   (2006.01)
*A61B 18/18*  (2006.01)

(52) U.S. Cl.
USPC ................... 607/154; 607/1; 607/2; 607/115; 607/150; 606/51; 606/52

(58) Field of Classification Search
USPC ............... 607/1, 2, 115, 150, 154; 606/51, 52
See application file for complete search history.

(56) References Cited

U.S. PATENT DOCUMENTS

| 6,273,887 | B1* | 8/2001 | Yamauchi et al. | 606/48 |
| 7,083,618 | B2* | 8/2006 | Couture et al. | 606/51 |
| 2004/0225287 | A1 | 11/2004 | Suzuki | |

FOREIGN PATENT DOCUMENTS

| JP | 5-5106 U | 1/1993 |
| JP | 2004-113546 A | 4/2004 |
| JP | 2004-524923 A | 8/2004 |
| JP | 2004-350938 A | 12/2004 |
| JP | 2006-518258 A | 8/2006 |

(Continued)

OTHER PUBLICATIONS

Abstract only of corresponding of Japanese Patent Application No. JP 2004-113328 A dated Apr. 15, 2004.

(Continued)

*Primary Examiner* — Niketa Patel
*Assistant Examiner* — Lindsey G Hankins
(74) *Attorney, Agent, or Firm* — Scully, Scott, Murphy & Presser, P.C.

(57) ABSTRACT

A high-frequency treatment instrument of the present invention includes: a pair of forceps members that includes a conductive electrode portion and an insulating portion and is supported by the forceps rotation shaft so as to be relatively rotatable; an operation section configured to open and close the pair of forceps members; a link mechanism that is attached to the pair of forceps members and includes a pair of link members; an operation wire that connects the link mechanism to the operation section; a rotation contact member that is rotatably connected to the pair of forceps members; and a regulation wire in which one end thereof is electrically connected to the rotation contact member, a part of an intermediate portion thereof is disposed so as to pass through a space between the respective link members, and the other end thereof is electrically connected to a power supply.

7 Claims, 12 Drawing Sheets

(56) References Cited

FOREIGN PATENT DOCUMENTS

| | | |
|---|---|---|
| JP | 4130943 A | 6/2008 |
| JP | 4197983 B2 | 12/2008 |
| WO | WO 02/080797 A1 | 10/2002 |

OTHER PUBLICATIONS

International Search Report PCT/JP2010/063393 dated Sep. 7, 2010.
Japanese Office Action dated Jun. 14, 2011 from corresponding Japanese Patent Application No. JP2011-513767 together with an English language translation.

* cited by examiner

HIGH-FREQUENCY TREATMENT INSTRUMENT

This application is a continuation application based on a PCT Patent Application No. PCT/JP2010/063393, filed Aug. 6, 2010, whose priority is claimed on Japanese Patent Application No. 2009-212945, filed on Sep. 15, 2009, the contents of both the PCT Application and the Japanese Application are incorporated herein by reference.

BACKGROUND OF THE INVENTION

1. Field of the Invention

The present invention relates to a high-frequency treatment instrument that is endoscopically inserted into a body cavity and is used by means of a high-frequency current supplied thereto.

2. Description of Related Art

Hitherto, there is a known treatment instrument for an endoscope (hereinafter, simply referred to as a 'treatment instrument') that performs various therapeutic techniques on tissue inside a body cavity of a patient or the like while being endoscopically inserted into the body cavity.

One type of the treatment instrument performs a treatment on target tissue using electric energy by means of a high-frequency current supplied to a treatment section in a distal end thereof, and is generally called a high-frequency treatment instrument (for example, see Japanese Patent (Granted) Publication No. 4197983).

In the high-frequency treatment instrument disclosed in the above patent document, a pair of forceps members supported through a rotation shaft so as to be relatively rotatable is installed at the distal end as the treatment section. The pair of forceps members is connected to an operation section on the hand side through an operation wire.

In many cases, the operation wire is formed of a conductor such as metal. For this reason, as a general configuration of the high-frequency treatment instrument, an operation wire is connected to a high-frequency power supply, and a high-frequency current is supplied to a treatment section such as a forceps member through the operation wire.

SUMMARY OF THE INVENTION

According to an aspect of the present invention, a high-frequency treatment instrument including: a pair of forceps members that includes a conductive electrode portion and an insulating portion and is supported by a rotation shaft so as to be relatively rotatable; an operation section configured to open and close the pair of forceps members; a link mechanism that is attached to the pair of forceps members and includes a pair of link members configured to rotate the respective forceps members around the rotation shaft; an operation wire that connects the link mechanism to the operation section; a rotation contact member that is rotatably connected to the pair of forceps members around the rotation shaft and is formed of a conductive member; and a power feeding wire in which one end thereof is electrically connected to the rotation contact member, a part of an intermediate portion thereof is disposed so as to pass through a space between the respective link members, and the other end thereof is electrically connected to a power supply capable of supplying electric power.

In addition, according to another aspect of the invention, a high-frequency treatment instrument including: a pair of forceps members, in which each of the forceps members includes a conductive electrode portion and an insulating portion and is supported by a rotation shaft so as to be relatively rotatable; an operation section configured to open and close the pair of forceps members; a link mechanism that is attached to the pair of forceps members and includes a pair of link members configured to rotate the respective forceps members around the rotation shaft; an operation wire that connects the link mechanism to the operation section; a rotation contact member that is rotatably connected to the pair of forceps members around the rotation shaft and is formed of a conductive member; and a power feeding wires in which one end thereof is electrically connected to the rotation contact member, a part of an intermediate portion thereof is disposed so as to pass through a space between the respective link members, and the other end thereof is electrically connected to a power supply capable of supplying electric power. Furthermore, the pair of forceps members is supported so that the respective electrode portions are insulated from each other by the insulating portion interposed between the respective electrode portions in the axial direction of the rotation shaft.

The link mechanism may include a connection member provided with a groove which extends in parallel to the axis of the operation wire. The power feeding wire may be disposed adjacent to the operation wire so as to be parallel to the operation wire in the side of operation section from the connection member. The connection member may guide the power feeding wire to the rotation contact member so as to separate the power feeding wire from the operation wire by disposing the power feeding wire inside the groove.

The electrode portion and the first end portion of the power feeding wire may be arranged so that at least a part of the electrode portion and the first end portion overlap each other when seen from the axial direction of the operation wire.

The rotation shaft may include a core body and an insulating layer that coats the outer peripheral surface of the core body.

The insulating layer may be configured as a cylindrical insulating member formed of an insulating material, and the insulating member includes a projecting portion that projects in the direction separating from the axis of the core body while being attached to the core body.

DETAILED DESCRIPTION OF THE INVENTION

Figure 1:
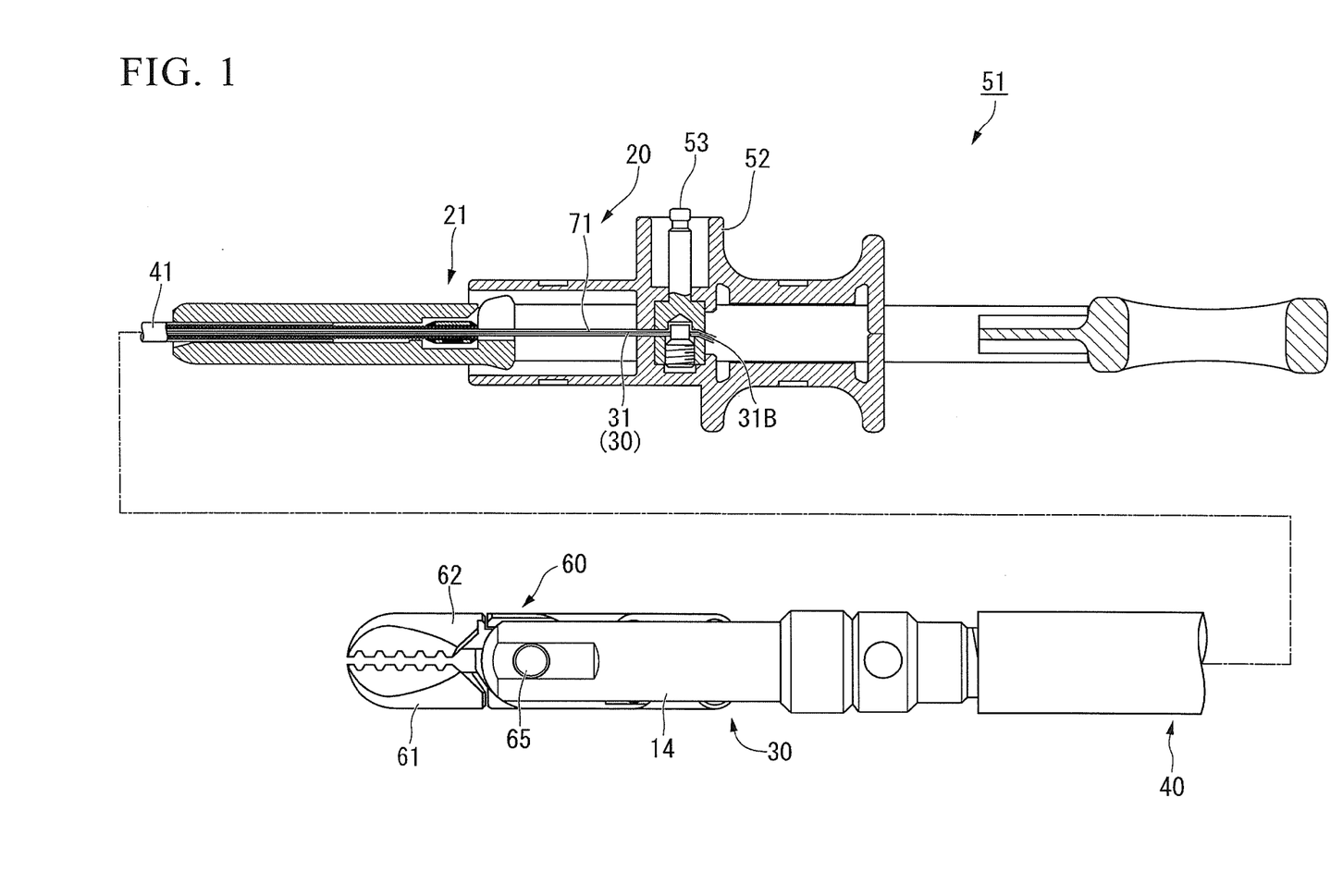
FIG. 1 is an entire diagram of a treatment instrument for an endoscope in a first embodiment of the present invention.

Hereinafter, referring to FIGS. 1 to 6, a treatment instrument for an endoscope in a first embodiment of the present invention will be described. As shown in FIG. 1, a high-frequency treatment instrument 51 in the present embodiment includes a treatment section 60 which is configured to perform a treatment on tissue inside a body cavity, an operation section 20 which is configured to operate the treatment section 60, a connection section 30 which is configured to connect the treatment section 60 to the operation section 20, and an elongated insertion section 40 which is inserted into the body cavity.

The treatment section 60 is configured such that a pair of forceps members including a first forceps member 61 and a second forceps member 62 is supported by a forceps rotation shaft (a rotation shaft) 65 so as to be relatively rotatable to each other. The forceps rotation shaft 65 is supported by a cover 14 which is disposed so as to interpose the forceps members 61 and 62 therein.

Figure 2:
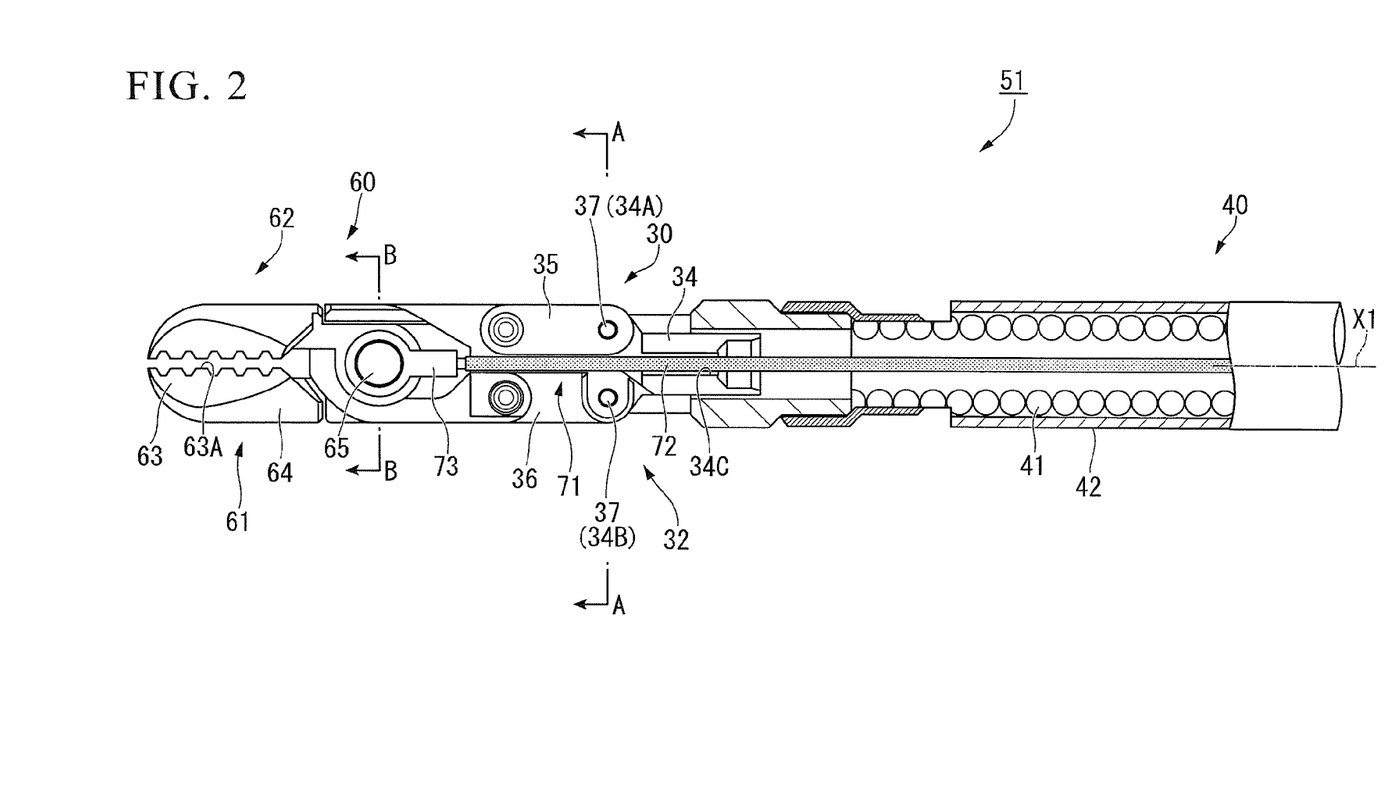
FIG. 2 is a diagram showing the periphery of a treatment section of the treatment instrument for the endoscope except a cover.

FIG. 2 is a diagram showing the periphery of the treatment section 60 of the high-frequency treatment instrument 51 except the cover 14. The second forceps member 62 is formed of a ceramic member such as alumina or zirconia or a resin such as polytetrafluoroethylene (PTFE) or polyether ether ketone (PEEK: registered trademark), and has an insulating property.

Furthermore, instead of such a configuration, the second forceps member 62 may be formed by coating an entire surface of a core formed of metal such as stainless steel or the like with the above-described insulating member, an insulating coating, or the like.

On the other hand, the first forceps member 61 includes an electrode portion 63 in which an electrode surface 63A thereof formed of a conductor such as stainless steel or the like is exposed and an insulating portion 64 which is placed so as to coat a part of the electrode portion 63. As shown in FIG. 2, it is desirable to provide the electrode surface 63A on at least an opening and closing surface which comes into contact with tissue inside a body cavity during a treatment and in which the pair of forceps members 61 and 62 face each other. Further, it is desirable that the area of the electrode surface 63A is small so that energy may be more easily concentrated.

The insulating portion 64 can be formed by performing a coating or an insulating coating on a part of the surface of the electrode portion 63 using the same insulating member as that of the second forceps member 62. The insulating portion 64 is placed so as to coat all portions of the electrode portion 63 having a possibility of coming into contact with, for example, the respective members of the connection section 30 to be described later or the cover 14 so that the current supplied to the electrode portion 63 does not leak to a metal portion such as the treatment section 60 and the connection section 30 and the like. Thus, in the first forceps member 61, almost all surfaces of the portion positioned at the base end side in relation to the forceps rotation shaft 65 to be described later are coated by the insulating portion.

Figure 3:
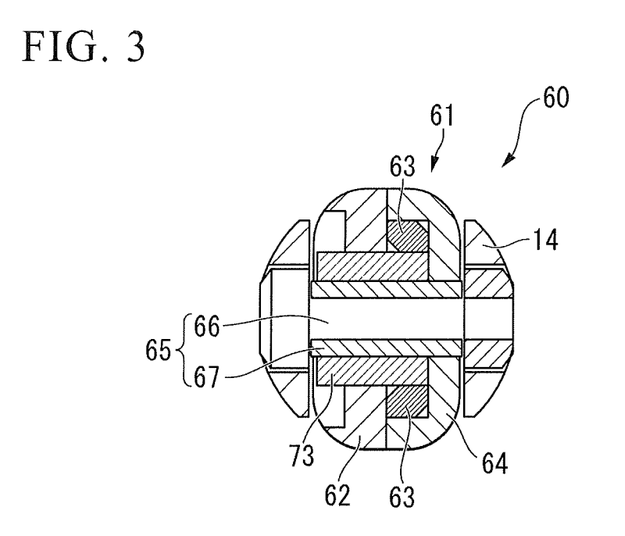
FIG. 3 is a cross-sectional view taken along the line B-B of FIG. 2.

FIG. 3 is a cross-sectional view taken along the line B-B of FIG. 2. As shown in FIG. 3, the forceps rotation shaft 65 connects the forceps members 61 and 62 to each other so as to be relatively rotatable. The forceps rotation shaft 65 includes a core body 66 formed of a conductor and a cylindrical portion (an insulating layer) 67 which coats the outer peripheral surface of the core body 66 for the purpose of insulation thereof. The cylindrical portion 67 may be formed as a member using an insulating material, or as an insulating layer using an insulating coating or the like.

Returning to FIG. 1, the operation section 20 includes a main body 21 to which the insertion section 40 is attached and a slider 52 which is slidably attached to the main body 21. The slider 52 is provided with a plug 53 which is connected to a high-frequency power supply (not shown).

The slider 52 and the treatment section 60 are connected to each other by the connection section 30, and the pair of forceps members 61 and 62 can be opened and closed by sliding the slider 52 in the longitudinal direction of the main body 21. This point will be specifically described in the description of the operation in use.

Figure 4:
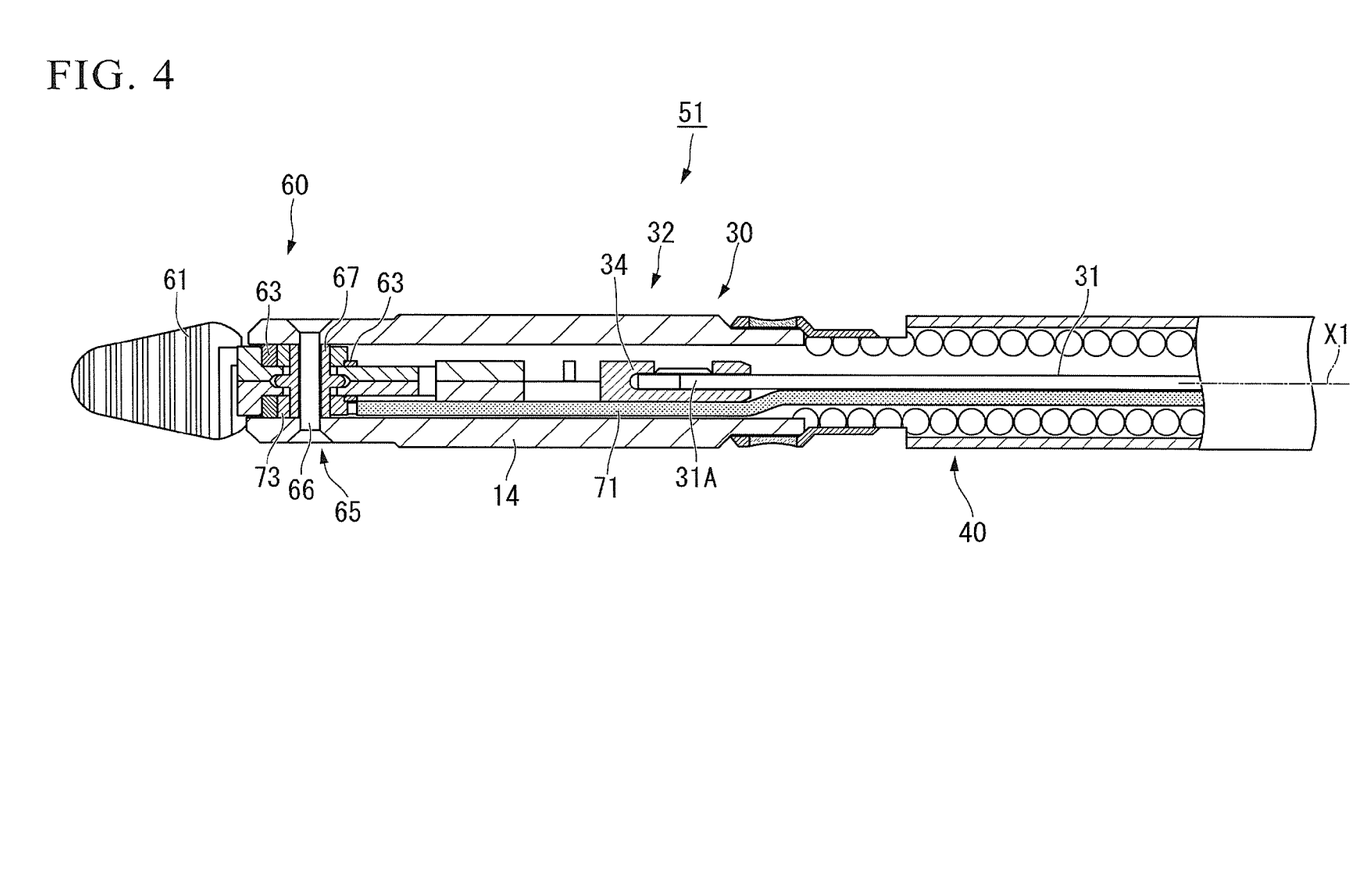
FIG. 4 is a cross-sectional view of the periphery of the treatment section.

FIG. 4 is a cross-sectional view of the periphery of the treatment section 60 which is seen from a different angle (the direction orthogonal to both the forceps rotation shaft 65 and the axis X1 of an operation wire 31). As shown in FIGS. 2 and 4, the connection section 30 includes the operation wire 31, a link mechanism 32 which is attached to the distal end of the operation wire 31, and a regulation wire (a regulation portion) 71 which guides reciprocating operation of the link mechanism 32. The operation wire 31 has a known configuration, where a first end portion 31A positioned at the distal end side thereof is connected to the link mechanism 32 and a second end portion 31B (see FIG. 1) positioned at the base end side thereof is connected to the slider 52 of the operation section 20.

The link mechanism 32 includes a connection member 34 which is attached to the distal end of the operation wire 31, and a first link member 35 and a second link member 36, as a pair of link members, used to connect the connection member 34 to the pair of forceps members 61 and 62 respectively.

The connection member 34 includes two link rotation shafts 34A and 34B which are provided at the distal end side thereof. The respective base ends of the first link member 35 and the second link member 36 are connected to the link rotation shafts 34A and 34B through pins 37 so as to be rotatable. Further, the connection member 34 is provided with a groove 34C which extends in parallel to the axis X1 of the operation wire 31.

The respective link rotation shafts 34A and 34B are spaced from the axis X1 of the operation wire 31 by the same distance (also substantially the same distance), and face each other with the axis X1 interposed therebetween. The axes of two pins 37 are parallel (also substantially parallel) to each other, and two link rotation shafts 34A and 34B are disposed so as to be parallel to each other.

The respective distal end sides of the link members 35 and 36 are connected to the base end sides of the first forceps member 61 and the second forceps member 62 so as to be rotatable. The positions of the respective link members 35 and 36 are set so as to be parallel to each other while the pair of forceps members 61 and 62 is closed.

The base end side (the second end portion) of the regulation wire 71 is electrically connected to the plug 53 of the operation section 20 through the insertion section 40, and the regulation wire 71 also serves as a power feeding wire which supplies a high-frequency current to the electrode portion 63 of the treatment section 60. The regulation wire 71 is provided with an insulating coating 72 throughout the substantially entire length thereof except both end portions so that a current does not leak to any metal portion except the electrode portion 63. Further, the regulation wire 71 is disposed in parallel (also substantially parallel) to the axis X1 of the operation wire 31 so as to pass inside the groove 34C of the connection member 34.

A cylindrical rotation contact member 73 is provided on the distal end (the first end portion) of the regulation wire 71. As shown in FIG. 3, the rotation contact member 73 is fitted to the outside of the cylindrical portion 67 so as to be coaxial with the forceps rotation shaft 65. The rotation contact member 73 is electrically connected to a part of the electrode portion 63 which is exposed so as to face the outer peripheral surface of the cylindrical portion 67.

As shown in FIG. 4, a part of the electrode portion 63 is disposed so as to be able to come into contact with the rotation contact member 73 at each of both sides of the rotation contact member 73 in the direction of the axis X1. That is, the rotation contact member 73 and the electrode portion 63 are arranged with a positional relationship in which at least a part of the rotation contact member 73 and a part of the electrode portion 63 overlap each other when seen in the direction of the axis X1.

With the above-described structure, the distal end of the regulation wire 71 is attached to the forceps rotation shaft 65 so as to be rotatable relative to the forceps rotation shaft 65, and is configured to supply a high-frequency current only to the electrode portion 63 of the first forceps member 61. Further, as shown in FIG. 2, the regulation wire 71 is disposed so as to be positioned between the first link member 35 and the second link member 36 when seen in the axial direction of the link rotation shafts 34A and 34B. That is, the regulation wire 71 and the respective link members 35 and 36 have a positional relationship in which they do not overlap each other when seen in the axial direction.

With the above-described respective structures, the high-frequency treatment instrument 51 is configured to serve as a monopolar (monopole type) high-frequency treatment instrument as a whole.

Figure 5:
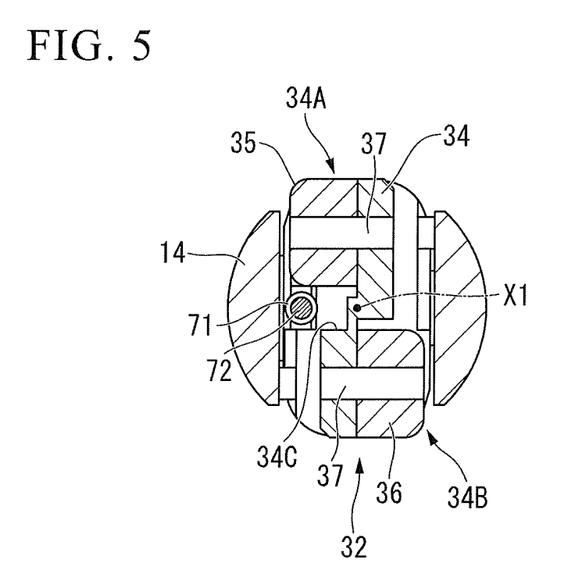
FIG. 5 is a cross-sectional view taken along the line A-A of FIG. 2.

FIG. 5 is a cross-sectional view taken along the line A-A of FIG. 2. As shown in FIG. 5, the cross-sectional shape of the connection member 34 in the plane orthogonal to the axis X1 is formed in a crank shape so that the portion provided with the link rotation shaft 34A and the portion provided with the link rotation shaft 34B are alternatively placed in relation to the axis X1 interposed therebetween. Accordingly, in either of the link rotation shafts 34A and 34B, the maximal value of the thickness of the link mechanism 32 is substantially equal to the sum of the thickness of the connection member 34 and the thicknesses of the link member 35, or is substantially equal to the sum of the thickness of the connection member 34 and the thicknesses of the link member 36. That is, the maximal value is suppressed to be a thickness corresponding to the two members.

As shown in FIG. 2, the insertion section 40 includes a coil sheath 41 through which the operation wire 31 is inserted and a tube sheath 42 through which the coil sheath 41 is inserted.

With regard to the coil sheath 41, variously known members may be appropriately selected and adopted. The cover 14 is attached to the distal end of the coil sheath 41, and the base end of the coil sheath 41 is fixed to the main body 21 of the operation section 20.

Figure 6:
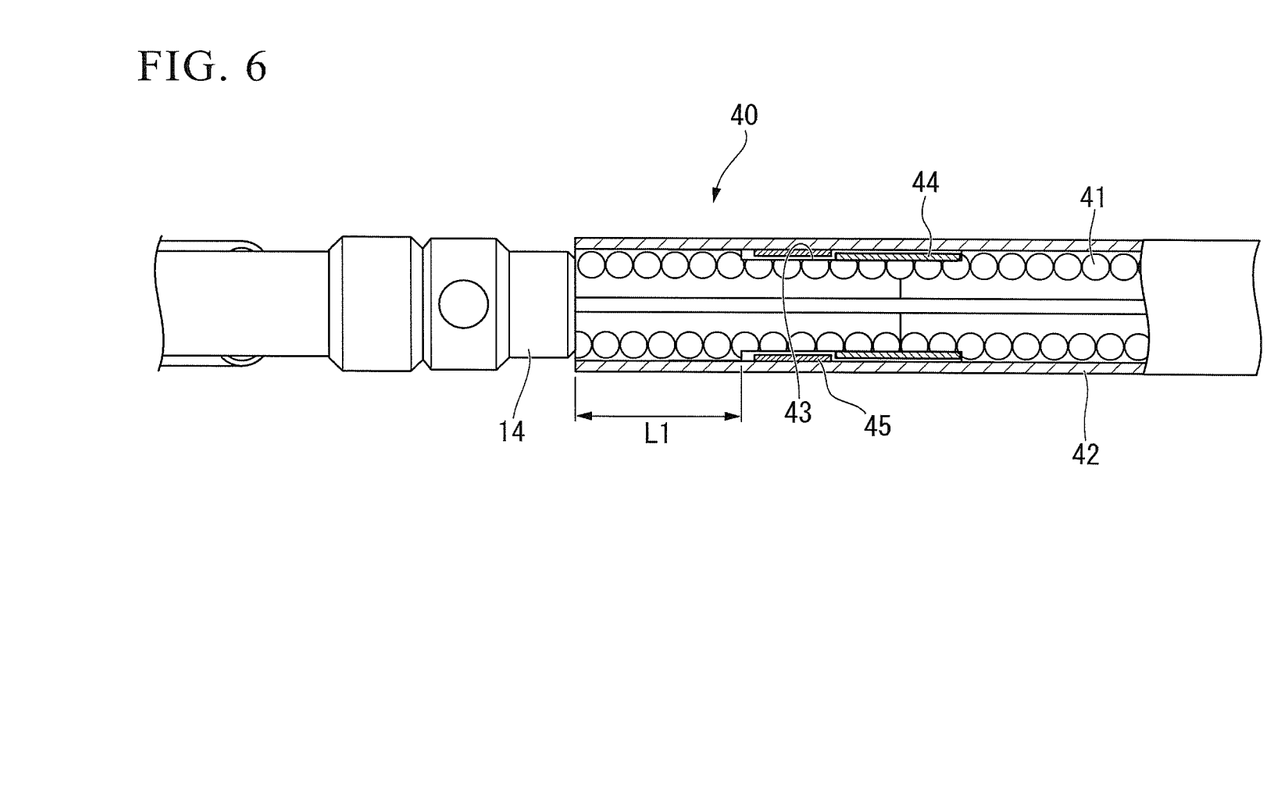
FIG. 6 is a cross-sectional view showing a part of an insertion section of the treatment instrument for the endoscope.

As shown in FIG. 6, the coil sheath 41 is provided with a small diameter portion 43 with a small outer diameter. The small diameter portion 43 is formed by performing a cutting process or the like on the outer peripheral surface of the coil sheath 41. The small diameter portion 43 is placed in the base end side portion away from the distal end of the coil sheath 41 by a predetermined length L1. The coil sheath 41 is divided into two parts at the small diameter portion 43, and an integral coil sheath is obtained by fixing a connection ring 44 attached to the small diameter portion 43 by a method such as soldering or the like.

Also with regard to the tube sheath 42, variously known members formed of a resin or the like may be appropriately selected and adopted. The base end of the tube sheath 42 is inserted into an opening provided at the distal end of the main body 21, but is relatively rotatable with respect to the main body 21. A ring member (a reciprocation regulating member) 45 which is fitted to the small diameter portion 43 of the coil sheath 41 is press-inserted into the tube sheath 42. In the press-inserted state, the inner diameter of the ring member 45 is set to be smaller than either of the basic outer diameter of the coil sheath 41 (the outer diameter of the portion other than the small diameter portion 43) and the outer diameter of the connection ring 44. Further, the inner diameter of the ring member 45 is larger than the outer diameter of the small diameter portion 43, and a clearance is ensured therebetween.

With such a configuration, the coil sheath 41 and the tube sheath 42 are configured to be relatively rotatable to each other around the axis and to be not substantially relatively movable to each other in the axial direction. In order to realize the above-described configuration, one coil sheath provided with the small diameter portion 43 is divided into two parts by cutting the coil sheath at the small diameter portion 43. Then, the cut coil sheaths are connected as one part by using the connection ring 44 while the ring member 45 is fitted into the small diameter portion of the cut coil sheath of a distal end side. Subsequently, when the coil sheath 41 to which the ring member 45 is attached is inserted into the tube sheath 42 and the ring member 45 is press-inserted into the tube sheath 42, the insertion section 40 of the high-frequency treatment instrument 51 is completed.

The predetermined length L1 may be appropriately set. But it is desirable to set the length, for example, 20 mm or more, in which the insertion section 40 between the connection member 34 of the connection section 30 and the ring member 45 is sufficiently bendable in order to substantially shorten the length of a rigid portion (described later) in the distal end side of the high-frequency treatment instrument 51.

The operation in use of the high-frequency treatment instrument 51 with the above-described configuration will be described.

First, an endoscope (not shown) is inserted into a body cavity of a patient who comes into contact with a known return electrode (not shown), and the distal end of the endoscope is made to advance to the vicinity of tissue (target tissue) inside a body cavity of a treatment target.

Subsequently, the slider 52 is retracted with respect to the main body 21 of the operation section 20 so that the pair of forceps members 61 and 62 is closed, and the insertion section 40 is inserted into a forceps channel of the endoscope. Then, the treatment section 60 is projected from the distal end of the forceps channel. At this time, since the treatment section 60 disposed at the distal end of the high-frequency treatment instrument 51 and a part of the connection section 30 covered by the cover 14 are away from the portion of the insertion section 40 provided with the ring member 45 by the predetermined length L1, the insertion section 40 positioned therebetween maintains its flexibility. As a result, even when the endoscope is disposed in a meandering shape or the like inside the body cavity, the insertion section 40 can be satisfactorily bent in accordance with the shape of the endoscope, and the high-frequency treatment instrument 51 can be appropriately inserted into the forceps channel of the endoscope.

After the treatment section 60 is projected from the forceps channel, a user connects a high-frequency power supply (not shown) to the plug 53 through a power supply cable (not shown).

Figure 7:
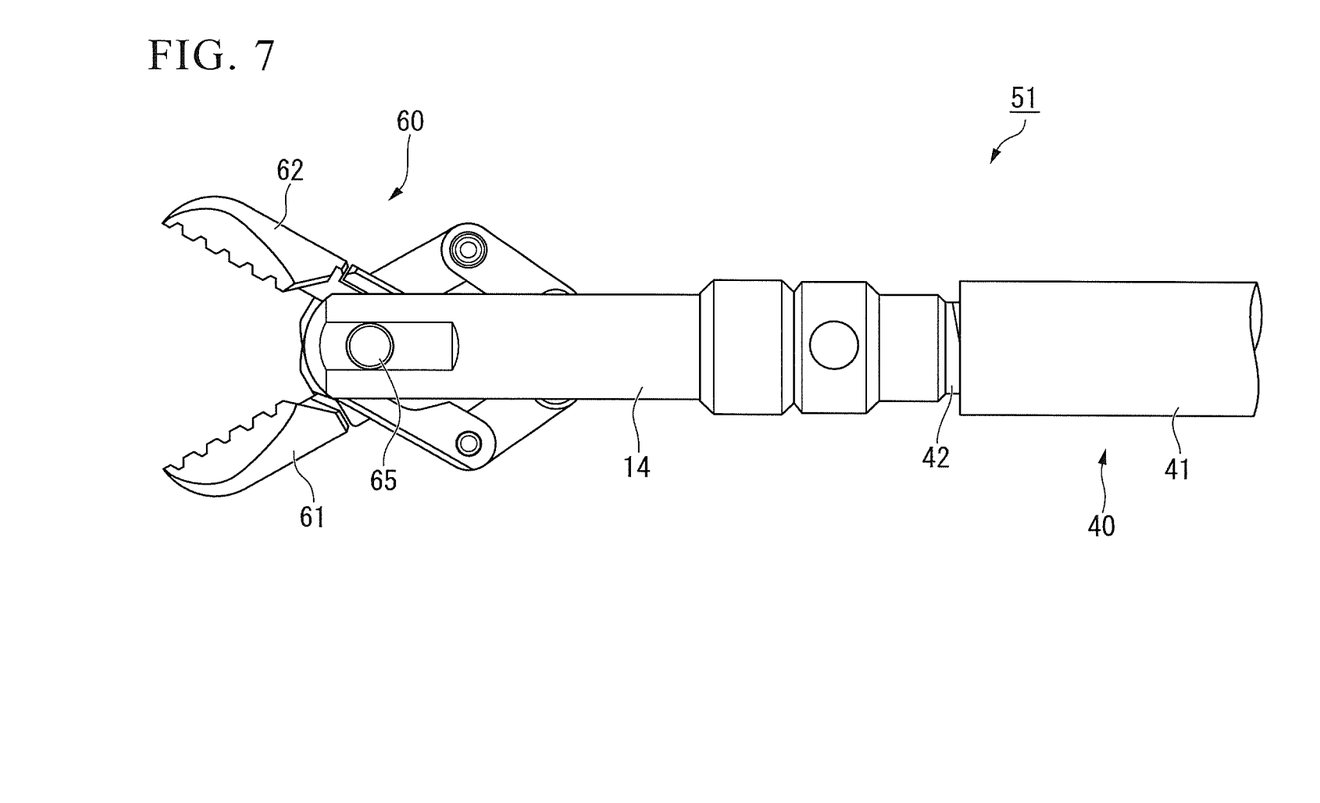
FIG. 7 is a diagram showing an operation when the treatment instrument for the endoscope is used.

When a treatment is performed, the slider 52 is moved forward with respect to the main body 21. Then, the operation wire 31 connected to the slider 52 advances with respect to the coil sheath 41. As described above, since the forceps rotation shaft 65 is supported by the cover 14 which is attached to the coil sheath 41, the first forceps member 61 and the second forceps member 62 respectively rotate around the forceps rotation shaft 65, so that the treatment section 60 is opened as shown in FIG. 7.

At this time, the operation wire 31 and the connection member 34 attached to the distal end thereof advance and retract along the regulation wire 71 which is disposed in parallel to the axis X1 of the operation wire 31 by allowing the groove 34C to engage with the regulation wire 71. Accordingly, the operation wire 31 and the connection member 34 are regulated in the relative movement direction with respect to the forceps rotation shaft 65, and the connection member 34 is operated to advance and retract while being suppressed from being deviated in the direction separating from the axis X1. As a result, the pair of forceps members 61 and 62 is satisfactorily opened and closed.

The user performs a desired treatment on target tissue while the pair of forceps members 61 and 62 of the treatment section 60 is opened and closed by sliding the slider 52. If necessary, the treatment section 60 may be rotated by rotating the main body 21 around the axis thereof so as to adjust a positional relationship between opening and closing surfaces of the pair of forceps members 61 and 62 and the target tissue.

When the user positions the target tissue between the pair of opened forceps members 61 and 62 of the treatment section 60 and pulls the slider 52 in the direction separating from the treatment section 60, the respective distal end sides of the pair of forceps members 61 and 62 are closed, so that the target tissue is nipped in the treatment section 60 and the electrode surface 63A comes into contact with the target tissue. In this state, when the user supplies a high-frequency current from the high-frequency power supply, the high-frequency current is supplied to the electrode portion 63 through the regulation wire 71, and the target tissue is cauterized at the electrode surface 63A.

After the completion of the treatment, the user extracts the high-frequency treatment instrument 51 from the forceps channel, extracts the endoscope to the outside of the body, and finishes the therapeutic technique.

According to the high-frequency treatment instrument 51 of the present embodiment, the regulation wire 71 is used as the power feeding wire. For this reason, compared to the case of the power feeding operation through the operation wire 31, an insulating may not be performed on the respective link members 35 and 36 and the like and the high-frequency current can be more easily and selectively supplied to the electrode portion 63. As a result, a power feeding structure can be realized in which energy more easily concentrates on the electrode surface 63A used for the treatment.

Further, since the distal end of the regulation wire 71 is connected to the forceps rotation shaft 65 so as to be relatively rotatable through the rotation contact member 73, no extra force is applied to the pair of forceps members 61 and 62 when the forceps members are opened and closed, and the forceps members can be appropriately opened and closed.

Furthermore, since the rotation contact member 73 does not move according to the operation in which the pair of forceps members 61 and 62 is opened and closed, the rotation contact member 73 is not exposed to the outside of the cover 14 during a treatment or the like. Accordingly, it is possible to appropriately prevent the regulation wire 71 from unnecessarily coming into contact with tissue inside a body cavity and leakage of electricity.

Furthermore, since the rotation contact member 73 is fitted to the outside of the cylindrical portion 67 of the forceps rotation shaft 65, the rotation contact member 73 is interposed between the cylindrical portion 67 and the electrode portion 63 which is exposed so as to face the outer peripheral surface of the cylindrical portion 67, and a part of the electrode portion 63 is disposed at each of both sides of the rotation contact member 73 in the direction of the axis X1. Accordingly, when the slider 52 is pulled to be away from the treatment section 60 so as to close the pair of forceps members 61 and 62 during a treatment, the regulation wire 71 is also pulled toward the operation section 20. In accordance with this operation, the rotation contact member 73 is also pulled toward the operation section 20 and is pressed against a part of the electrode portion 63. Accordingly, the rotation contact member 73 reliably comes into contact with the electrode portion 63, so that the high-frequency current can be supplied therethrough during a treatment.

Furthermore, the forceps rotation shaft 65 includes the core body 66 which is formed of a conductor such as metal and the cylindrical portion 67 which coats the outer peripheral surface of the core body 66 for the purpose of insulating thereof. Accordingly, the forceps rotation shaft 65 can easily ensure rigidity to sufficiently withstand a force applied thereto when the pair of forceps members 61 and 62 is operated to be opened and closed, while the insulation between the forceps rotation shaft 65 and the electrode portion 63 is maintained.

Further, since the regulation wire 71 serving as the power feeding wire and the pair of link members 35 and 36 are arranged so as not to overlap each other when seen from the axial direction of the link rotation shafts 34A and 34B, the regulation wire 71 can be disposed so as to pass between the pair of link members 35 and 36 arranged in parallel to each other and to have a linear shape parallel to the axis X1 of the operation wire 31. As a result, the regulation wire 71 can be appropriately equipped with both a function of guiding a sliding movement of the connection member 34 of the connection section 30 and a function of feeding power to the electrode portion 63.

Furthermore, the connection member 34 is provided with two link rotation shafts 34A and 34B which are spaced from the axis X1 of the operation wire 31, and the link rotation shafts 34A and 34B are connected to the first link member 35 and the second link member 36 respectively. Accordingly, the thickness of the connection portion of the connection member 34 and the respective link members 35 and 36 in the extension direction in which the respective link rotation shafts 34A and 34B extend is equal to the thickness corresponding to the sum of the connection member 34 and either of the link members 35 and 36 in all longitudinal range thereof. As a result, compared to an existing structure in which two link members are connected to one rotation shaft, the distal end side portion including the treatment section can be further decreased in diameter.

Further, the rigid treatment section 60 and a part of the connection section 30 which are provided at the distal end of the high-frequency treatment instrument 51 are arranged so as to be away by the predetermined length L1 from the ring member 45 which relatively rotatably connects the coil sheath 41 and the tube sheath 42 in the insertion section 40. For this reason, when the rigid treatment section 60 and the like are near the ring member 45, the length of the distal end side rigid portion of the treatment instrument 1 which corresponds to the sum of the lengths thereof in the axial direction can be substantially shortened. Accordingly, a high-frequency treatment instrument which has a satisfactory insertion property into the endoscope can be obtained.

In an existing high-frequency treatment instrument, the structure to relatively rotatably connect the coil sheath 41 to the tube sheath 42 is provided near the distal end of the tube sheath in many cases. As a result, there are problems in that the length of the distal end side rigid portion is long, the high-frequency treatment instrument is not easily inserted into the forceps channel, and large force is needed to insert and extract the high-frequency treatment instrument into and from the endoscope. The structure of the insertion section 40 of the high-frequency treatment instrument 51 of this embodiment solves these problems.

Next, the second embodiment of the present invention will be described by referring to FIGS. 8 to 10. A high-frequency treatment instrument 81 of this embodiment is different from the high-frequency treatment instrument 51 of the above-described first embodiment in that the high-frequency treatment instrument 81 is formed as a bipolar (dipole type) high-frequency treatment instrument as a whole.

Furthermore, in the description below, the repetitive description will be omitted by giving the same reference signs to the components similar to those of the high-frequency treatment instrument 51 of the first embodiment.

Figure 8:
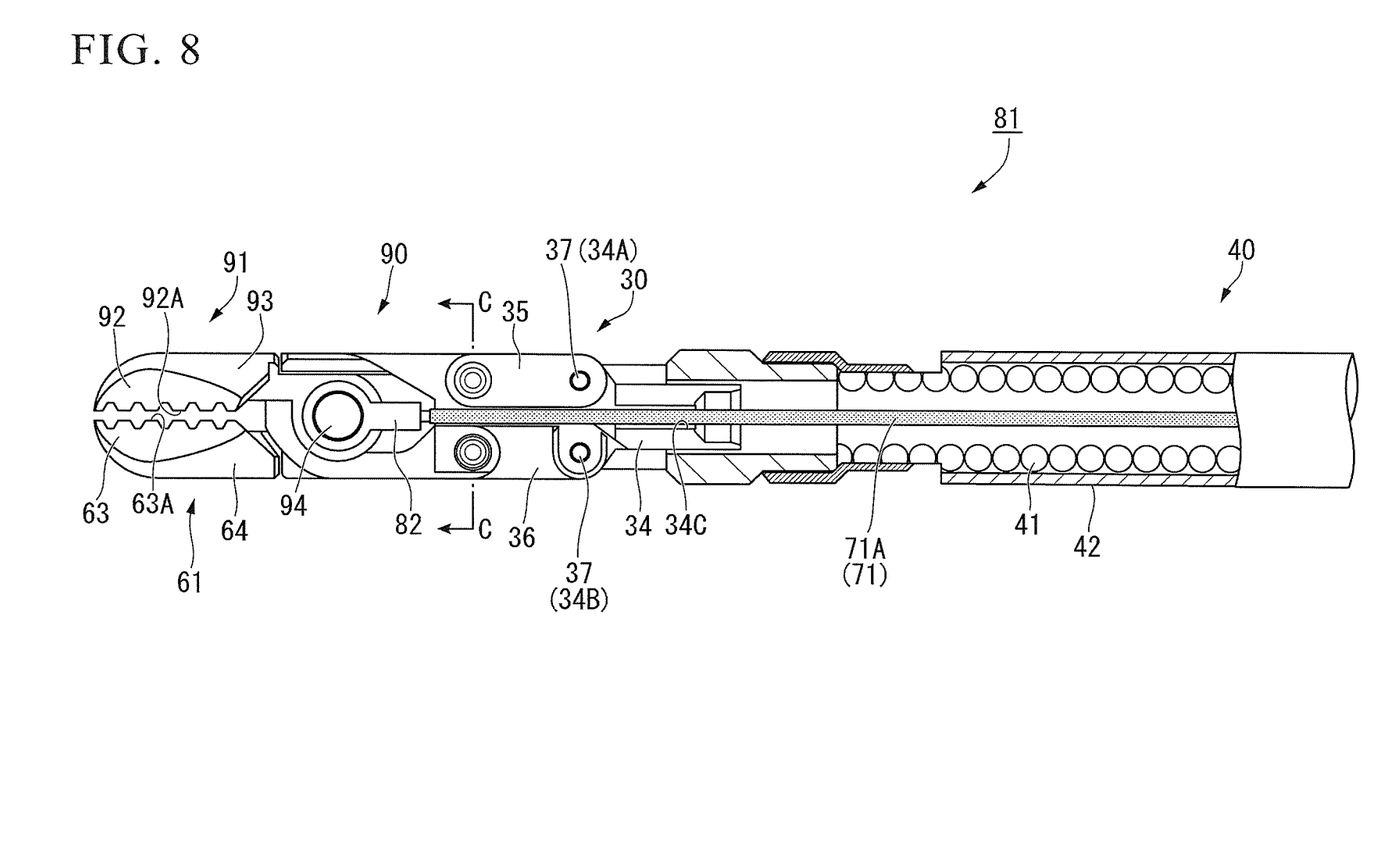
FIG. 8 is a diagram showing the periphery of a treatment section of a treatment instrument for an endoscope in a third embodiment of the present invention except a cover.
Figure 9:
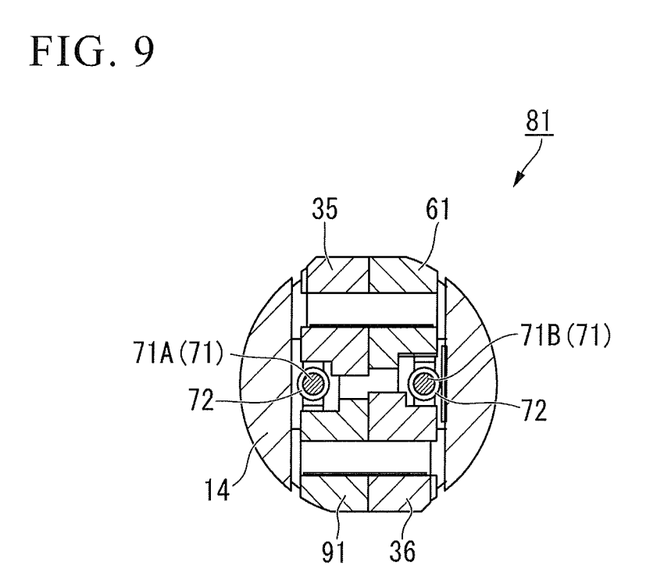
FIG. 9 is a cross-sectional view taken along the line C-C of FIG. 8.
Figure 10:
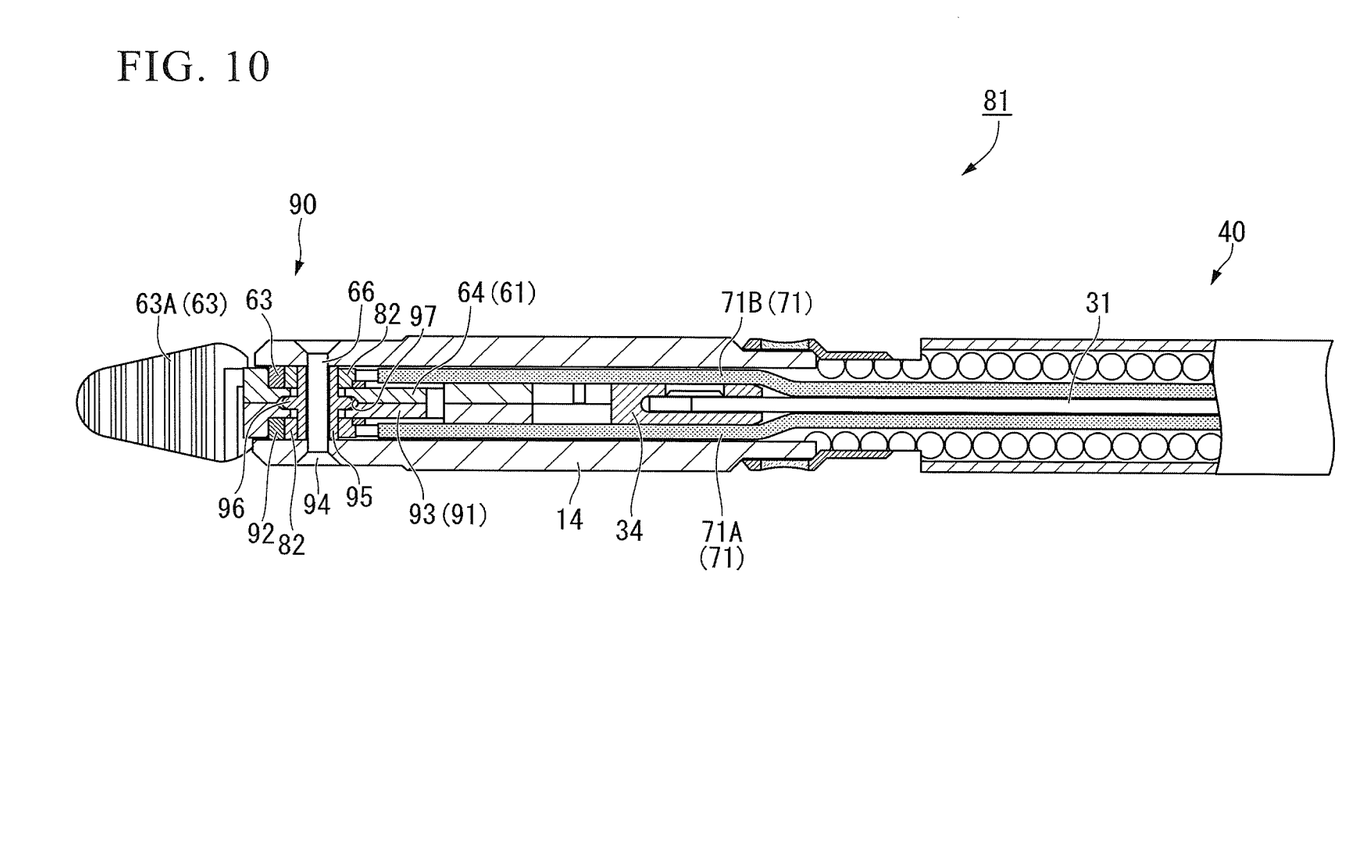
FIG. 10 is a cross-sectional view of the periphery of the treatment section.

FIG. 8 is a diagram showing the periphery of a treatment section 90 of a treatment instrument 81 except the cover 14, and FIG. 9 is a cross-sectional view taken along the line C-C of FIG. 8. Further, FIG. 10 is a cross-sectional view of the periphery of the treatment section 90 in the plane parallel to both the forceps rotation shaft and the operation wire. As shown in FIGS. 8 to 10, in the treatment instrument 81, two regulation wires 71 which also serve as the power feeding wire are connected to the treatment section 90. In accordance with this, the groove 34C is also provided on each of both sides of the connection member 34.

The treatment section 90 includes a pair of forceps members which serves as the first forceps member 61 and a second forceps member 91. The second forceps member 91 has the substantially same structure as that of the first forceps member 61, and includes an electrode portion 92 with an electrode surface 92A and an insulating portion 93. The contact portions of the first forceps member 61 and the second forceps member 91 are respectively coated by the insulating portions 64 and 93 so as not to be electrically connected to each other. For example, the insulating portion 64 of the first forceps member 61 and the insulating portion 93 of the second forceps member 91 are interposed between the electrode portion 63 of the first forceps member 61 and the electrode portion 92 of the second forceps member 91 along the axial direction of a forceps rotation shaft 94 to be described later. Accordingly, the pair of forceps members 61 and 91 is supported so as to be relatively rotatable to each other through the forceps rotation shaft 94 while the insulation thereof is ensured.

The forceps rotation shaft 94 includes the core body 66 and an insulating cylindrical portion 95. The outer peripheral surface of the cylindrical portion 95 is provided with a flange (a projecting portion) 96 which protrudes outward in the radial direction throughout the entire circumference. Each of the first forceps member 61 and the second forceps member 91 which are connected to the forceps rotation shaft 94 is provided with a notch in a facing surface to each other, and the flange 96 enters a concave portion 97 which is formed of the notches.

A rotation contact member 82 which is attached to two regulation wires 71 has the substantially same shape as that of the rotation contact member 73 of the first embodiment, but the length of the cylindrical portion which is fitted to the outside of the forceps rotation shaft 94 in the axial direction is set to be shorter than that of the rotation contact member 73. As shown in FIGS. 8 and 10, one regulation wire 71A is electrically connected to the electrode portion 92 of the second forceps member 91, and the other regulation wire 71B is electrically connected to the electrode portion 63 of the first forceps member 61. The respective base ends of the regulation wires 71A and 71B are connected to a high-frequency power supply (not shown), and form a high-frequency current circuit.

The method of using the high-frequency treatment instrument 81 is the same as that of the general bipolar high-frequency treatment instrument, and the installation of the return electrode is not needed. When the user nips the target tissue between the pair of forceps members 61 and 91 and supplies power to the treatment section 90, a high-frequency current flows from the electrode surface (for example, the electrode surface 63A) of one forceps member to the electrode surface (for example, the electrode surface 92A) of the other forceps member, so that the target tissue is cauterized.

In the high-frequency treatment instrument 81 of this embodiment, the same effects as that of the high-frequency treatment instrument 51 of the first embodiment can be also obtained, and a current-carrying treatment can be performed while the pair of forceps members is appropriately opened and closed.

Furthermore, the flange 96 is provided on the cylindrical portion 95 of the forceps rotation shaft 94, and the facing surfaces of the pair of forceps members 61 and 91 are provided with the concave portion 97. Accordingly, since the lateral distance of the member which is interposed between the electrode portion 63 of the first forceps member 61 and the electrode portion 92 of the second forceps member 91 becomes longer, a further reliable insulation can be performed therebetween.

As described above, the respective embodiments of the present invention have been described, but the technical scope of the invention is not limited to the above-described respective embodiments, and may be modified into various forms without departing from the technical scope.

For example, in the above-described respective embodiments, an example has been described in which the small diameter portion 43 is provided on the coil sheath 41 and the ring member 45 is attached to the small diameter portion 43 so that the coil sheath 41 and the tube sheath 42 are relatively rotatable and are not relatively movable in the axial direction. This structure has an advantage in that the coil sheath and the tube sheath can be assembled without increasing the diameter of the insertion section. However, instead of this structure, as shown in the modified example of FIG. 11, a stopper ring 46 which has an outer diameter larger than the inner diameter of the ring member 45A which is press-inserted into the tube sheath 42 may be attached to the outer periphery of the coil sheath 41 by soldering or the like so as to be positioned at each of both sides of the axial direction of the ring member 45A without forming the small diameter portion in the coil sheath 41.

Figure 11:
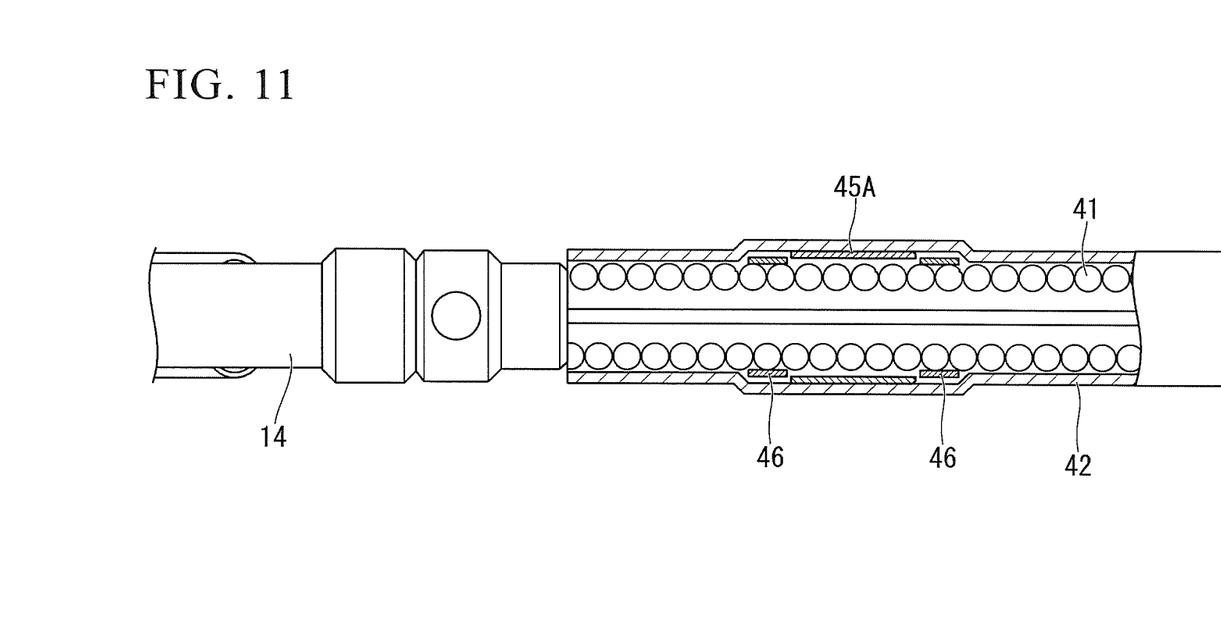
FIG. 11 is a cross-sectional view showing a part of an insertion section in a treatment instrument for an endoscope of a modified example of the present invention.

In this way, the diameter of the portion to which the ring member 45A or the stopper ring 46 is attached increases compared to the case of forming the small diameter portion. However, in the case of the treatment instrument or the like which is less restricted in the diameter, there are advantages in that the coil sheath 41 does not need to be cut and the coil sheath 41 and the tube sheath 42 can be easily assembled with a small number of processes.

Furthermore, in this case, a configuration may be adopted in which the dimensional relationship between the ring member 45A and the stopper ring 46 is reversed, the stopper ring 46 is press-inserted into the tube sheath, and the ring member 45A is fixed to the coil sheath 41.

Further, in the above-described respective embodiments, an example has been described in which a regulation portion that regulates the rotation of the connection member around the axis is formed of the regulation wire. In the case where the regulation wire is not used as the power feeding wire, instead of this configuration, as shown in the modified example of FIG. 12, a protrusion 14A may be formed on the cover 14 so as to protrude toward the connection member 34, and the protrusion 14A may engage with the groove 34C of the connection member 34 so as to regulate the rotation of the connection member and the operation wire around the axis.

Figure 12:
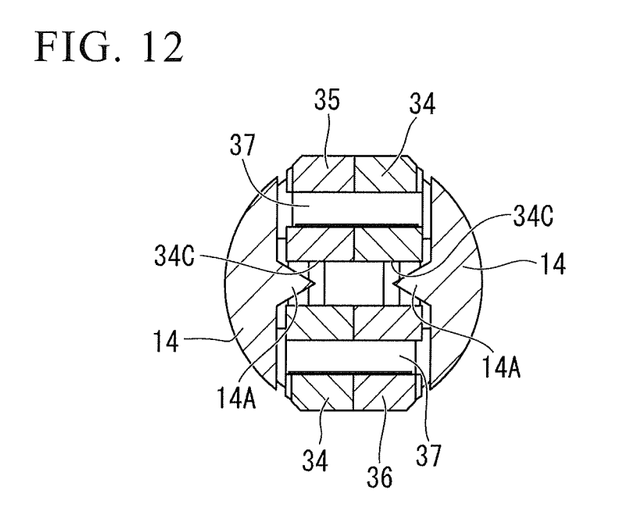
FIG. 12 is a cross-sectional view of a connection section in a treatment instrument for an endoscope of a modified example of the present invention.

At this time, a pair of the protrusion 14A and the groove 34A may be, of course, provided only at one side.

Furthermore, the shape of the connection member which is provided at the distal end of the operation wire is also not limited to that of the above-described respective embodiments. For example, one link rotation shaft may be provided and the respective base ends of the pair of link members may be connected to the link rotation shaft.

Further, the pair of link members connected to two link rotation shafts may be arranged so as to intersect each other while the pair of forceps members is closed.

Furthermore, the structures and the configurations of the above-described respective embodiments may be appropriately combined with each other.

According to the present invention, a high-frequency treatment instrument with a power feeding structure capable of easily concentrating energy can be provided.

The invention claimed is:

1. A high-frequency treatment instrument comprising:
    a pair of forceps members that includes a conductive electrode portion and an insulating portion and is supported by a rotation shaft so as to be relatively rotatable;
    an operation section configured to open and close the pair of forceps members;
    an operation wire that transmits an operation input to the operation section to the pair of forceps members;
    a connection member provided at a distal end of the operation wire and having a pair of link rotation shafts;
    a pair of link members that includes a first link member and a second link member, being arranged parallel when the pair of the forceps members is closed and capable of moving in a direction separating from each other, in which each first end portion of the first and second link members is rotatably connected to each proximal end portion of the pair of forceps members, and each second end portion of the first and second link members is rotatably connected to each of the pair of link rotation shafts; and
    a rotation contact member that is rotatably connected to the pair of forceps members around the rotation shaft and is formed of a conductive member;
    wherein
    a first space is formed between the first and second link members when they are arranged parallel to each other, and is provided outside of movement range of these link members,
    a second space is formed between the pair of the link rotation shafts,
    a power feeding wire is provided, in which one end thereof is electrically connected to the rotation contact member, a part of an intermediate portion of the power feeding wire is disposed so as to pass through the first space and the second space, and the other end thereof is electrically connected to a power supply capable of supplying electric power,
    each of the link rotation shaft is separated from an axis of the operation wire by the same distance and faces with each other interposing the axis, and
    the power feeding wire and the pair of link members are arranged so as not to overlap each other when seen from an axial direction of the pair of link rotation shafts.

2. The high-frequency treatment instrument according to claim 1, wherein the pair of forceps members is supported so that their electrode portions are insulated from each other by the insulating portion interposed between the electrode portions in an axial direction of the rotation shaft.

3. The high-frequency treatment instrument according to claim 2, wherein the electrode portions and the first end portion of the power feeding wire are arranged so that at least a part of the electrode portions and the first end portion overlap each other when seen from an axial direction of the operation wire.

4. The high-frequency treatment instrument according to claim 1, wherein
    the connection member has a groove which extends in parallel to an axis of the operation wire,
    the power feeding wire is disposed adjacent to the operation wire so as to be parallel to the operation wire in a side of the operation section from the connection member, and
    the connection member guides the power feeding wire to the rotation contact member so as to separate the power feeding wire from the operation wire by disposing the power feeding wire inside the groove.

5. The high-frequency treatment instrument according to claim 1, wherein the rotation shaft includes a core body and an insulating layer that coats an outer peripheral surface of the core body.

6. The high-frequency treatment instrument according to claim 5, wherein the insulating layer is configured as a cylindrical insulating member formed of an insulating material, and the insulating member includes a projecting portion that projects in a direction separating from an axis of the core body while being attached to the core body.

7. The high-frequency treatment instrument according to claim 1, wherein the pair of forceps members is opened when the pair of link members rotates so that each first end portion separates.

* * * * *